United States Patent [19]

Van Gogh

[11] Patent Number: 5,072,059
[45] Date of Patent: Dec. 10, 1991

[54] TWO-STEP MONOETHYLENE GLYCOL PREPARATION PROCESS

[75] Inventor: Johan Van Gogh, Amsterdam, Netherlands

[73] Assignee: Shell Oil Company, Houston, Tex.

[21] Appl. No.: 612,371

[22] Filed: Nov. 14, 1990

[30] Foreign Application Priority Data

Mar. 15, 1990 [GB] United Kingdom ............... 9005814

[51] Int. Cl.$^5$ .................. C07C 29/10; C07C 31/20
[52] U.S. Cl. ................................ 568/866; 568/386; 568/867
[58] Field of Search ................. 568/866, 867, 386

[56] References Cited

U.S. PATENT DOCUMENTS

| 2,122,813 | 7/1938 | Gvoll et al. | 568/866 |
| 4,069,261 | 1/1978 | Kyo et al. | 568/866 |
| 4,368,337 | 1/1983 | Tawers et al. | 568/866 |

FOREIGN PATENT DOCUMENTS

| 474785 | 6/1951 | Canada | 568/386 |
| 1086241 | 9/1959 | Fed. Rep. of Germany . | |
| 1177877 | 1/1970 | United Kingdom | 568/867 |
| 2023601 | 1/1980 | United Kingdom | 568/867 |
| 2098985 | 7/1982 | United Kingdom . | |

Primary Examiner—J. E. Evans

[57] ABSTRACT

A two-step reaction process for converting ethylene oxide with high selectivity into monoethylene glycol which comprises firstly reacting ethylene oxide with acetone in the presence of a solid acid catalyst to form 2,2-dimethyl-1,3-dioxolane and secondly hydrolyzing the 2,2-dimethyl-1,3-dioxolane with water in the presence of a solid acid catalyst to form monoethylene glycol.

8 Claims, No Drawings

TWO-STEP MONOETHYLENE GLYCOL PREPARATION PROCESS

FIELD OF THE INVENTION

The invention relates to a two-step reaction process for converting ethylene oxide with high selectivity into monoethylene glycol.

BACKGROUND OF THE INVENTION

It is generally known that monoethylene glycol is prepared by reaction of ethylene oxide with water at a temperature between 180° C. and 220° C., wherein the amount of water is about 10 times the amount of ethylene oxide (by weight). Disadvantages of the process are that large amounts of water must be flashed off and still considerable amounts of diethylene glycol are prepared. The use of a catalyst may lead to a reduction in the amount of water (but not to stoichiometric amount), but the amount of diethylene glycol is hardly diminished.

A process for the preparation of monoethylene glycol has now been found which does not have these disadvantages.

It is an object of the invention to prepare monoethylene glycol from ethylene oxide in very high yield.

It is another object of the invention to use as little water as possible.

SUMMARY OF THE INVENTION

According to the invention, ethylene oxide is converted with high selectivity into monoethylene glycol in a two-step reaction process which comprises first reacting ethylene oxide with acetone in the presence of a solid acid catalyst to form 2,2-dimethyl-1,3-dioxolane and thereafter hydrolyzing the 2,2-dimethyl-1,3-dioxolane with water in the presence of a solid acid catalyst to form monoethylene glycol.

DESCRIPTION OF THE PREFERRED EMBODIMENTS

In the German "Auslegesschrift" 1,086,241 is disclosed the preparation of 1,3-dioxolanes by reacting epoxy compounds with carbonyl compounds in the presence of acid activated bentonite. The reaction between acetone and ethylene oxide has been mentioned and the yield of this step is 83 percent. Reactions with other compounds give similar yields. The publication does not teach how the objects of our invention could be fulfilled.

In the United Kingdom Patent No. 2,098,985 is disclosed a two-step process whereby an alkylene oxide reacts with carbon dioxide in the presence of a phosphonium halide, there being substantially less than an equimolar amount of water present based on the ethylene oxide, to produce an alkylene carbonate, which latter product is reacted with water in the presence of the same phosphonium halide to a glycol. This two-step process has the disadvantages that rather high temperatures (180° C.) and no solid catalyst is used.

Solid acidic catalysts, to be employed in the process according to the invention are acid activated clays. They are especially suitable for the reaction of ethylene oxide with acetone into 2,2-dimethyl-1,3-dioxolane. Especially important clays are those of the montmorillonite series, such as montmorillonite, beidellite, nontronite, hectorite, saponite and sauconite. Acid activated clays are the clays which have been treated with mineral acids, such as hydrochloric acid or sulphuric acid. The acid activated clays are prepared by mixing crushed raw material with water to form a slurry to which the mineral acid amounting to about 35% of the total dry weight of the clay is added. The mixture is then treated with live steams for 5 to 6 hours, after which the whole mixture is dumped into fresh water and then washed, until it is substantially free of acids.

The mol ratio of acetone to ethylene oxide may range from 1:1 to 5:1, although higher ranges are not excluded.

Since the reaction of acetone with ethylene oxide is exothermic, the temperature is regulated by refluxing the acetone. At a later stage a somewhat higher temperature than the boiling temperature of acetone is suitable. The reaction temperature generally ranges from 30° C. to 80° C., preferably from 50° C. to 65° C.

In the hydrolyzing step either the raw mixture or purified 2,2-dimethyl-1,3-dioxolane may be used. Since 2,2-dimethyl-1,3-dioxolane boils at 92° C., the compound can be purified by distillation. Hydrolysis of the 2,2-dimethyl-1,3-dioxolane in the second step is done in the presence of water with the aid of an acid activated clay or an ion-exchange resin. About the stoichiometric amount of water is sufficient to obtain substantial hydrolysis of the 2,2-dimethyl-1,3-dioxolane into monoethylene glycol and acetone. During this reaction the formed acetone is distilled off and any unreacted ketal may be recycled.

The invention will now be further described by the following examples which are intended to be illustrative and are not intended to be construed as limiting the scope of the invention.

EXAMPLES

A. Preparation of the cyclic ketal 2,2-dimethyl-1,3-dioxolane

For the preparation of the ketal a glass, double walled reactor with a content of 2 liters was used and was provided with a glass stirrer and four glass joints for placing a thermocouple well, two gas inlet tubes and a reflux condenser. One of the gas inlet tubes was used for a slight nitrogen purge, the other one (both made from glass) was connected via a ball joint connection to the steel exit tube of a syringe pump (type LC-5000 from Isco Inc.) containing the stock of liquid ethylene oxide under a pressure of 15–20 bar. Water was circulated around the wall of the glass reactor via a thermostatted bath for heating/cooling purposes.

The reactor was charged with 1695 ml (1340 g, 23.1 mol) of acetone and 34 g of K10 catalyst (acid activated montmorillonite, supplied by Sued-Chemie) and the suspension thus obtained was heated under stirring to 54° C. At this stage the introduction of liquid ethylene oxide from the syringe pump was started, an amount of 305 ml (269 g, 6.1 mol) being introduced in the course of 45 minutes. By means of a valve in the steel exit tube of the Isco pump, a pressure in the latter of 15–20 bar was maintained to keep the ethylene oxide in the liquid form. At 54° C., the formation of the cyclic ketal started immediately, the heat of reaction being removed via refluxing of the excess of acetone; the boiling point of reaction mixture gradually increased over the period of ethylene oxide addition (due to formation of the cyclic ketal, bp. 92° C.) from 56° C. to 62° C.

After a post reaction of 15 minutes, the reaction mixture was cooled and the K10 catalyst allowed to settle after which the supernatant liquid was sucked by slight vacuum from the catalyst layer. A new batch of acetone was then charged to the reactor and the reaction repeated. The amounts of acetone and ethylene oxide were the same as described above along with the original amount of K10 catalyst, which was thus reused.

Twelve batch reactions were carried out according to the procedure described above. The combined product (18.42 kg) in which no ethylene oxide could be detected had the following composition (GC analysis):

| | |
|---|---|
| acetone | 60.7% w |
| ketal | 38.9% w |
| monoethyleneglycol | 0.1% w |
| diethyleneglycol | 0.2% w |
| 1,4-dioxane | 0.1% w |

B. Hydrolysis of the cyclic ketal

Two options were carried out by addition of water and acid catalyst either to the reaction mixture prepared under A or to the ketal isolated prior to the hydrolysis step.

The equipment used was a 10 l distillation flask provided with a fractionating Vigreux column of approx. 6 m length having 15–20 theoretical plates.

1. Hydrolysis of the reaction mixture

Into the distillation flask were present the following components: reaction mixture prepared according to method under A: 6000 g

| | |
|---|---|
| water | 452 g water/ketal mol ratio 1.09 |
| Amberlyst 15 | 10 g |

The acid ion exchange resin catalyst Amberlyst 15 (styrene-divinylbenzene copolymer containing sulphonic acid groups) was wrapped in glass cloth and placed into the distillation flask in order to prevent crushing during boiling of the reaction mixture. The excess of acetone as well as the amount of acetone from the hydrolysis of the ketal was distilled at atmospheric pressure. When the bulk of the ketal had been converted into glycol and acetone, the boiling point started to rise sharply but was maintained at 110° C. to protect the catalyst. Further conversion of the ketal was then carried out under a pressure of 250 mbar until distillation of the acetone stopped. The following mass balance was obtained:

| | In (g) | | Out (g) | |
|---|---|---|---|---|
| ketal | 2352 | (23.1 mol) | 31.8 | (0.3 mol) |
| monoethylene glycol | 17.4 | (0.3 mol) | 1414.7 | (22.8 mol) |

| | In (g) | Out (g) |
|---|---|---|
| total mass | 6452 | 6445 |

Thus, the total mass balance was 99.9% and the mol balance of MEG+ketal 98.7%.

This result points to a catalyst consumption of less than 1% by weight of monoethylene glycol.

2. Hydrolysis of the cyclic ketal isolated from the reaction mixture

An amount of 5212 g of the reaction mixture (prepared according to method under A) was distilled in order to isolate the bulk of the ketal. A distilled fraction of 2036 g containing 89.6% w ketal (17.88 mol), 10.3% w acetone and about 0.2% w 1,4-dioxane was combined with 355 g H$_2$O (mol ratio H$_2$O/ketal 1.1) and 20 g of Amberlyst 15 (wrapped in glass cloth). Because the liquid mixture consisted of two phases, it was homogenized at room temperature by a shift of equilibrium before being introduced with the catalyst in the distillation flask.

Equilibration and distillation of the acetone (basically the same procedure as applied in the first hydrolysis under 1) yielded ultimately a residue containing 1091 g monoethylene glycol (17.6 mol) and traces of acetone, unconverted ketal and 1,4-dioxane but no heavy glycols. The mol balance on monoethylene glycol and total unconverted ketal (0.12 mol) was 99%, the same figure being found for the total mass balance.

What is claimed is:

1. A two-step reaction process for converting ethylene oxide with high selectivity into monoethylene glycol which comprises a) reacting ethylene oxide with acetone in the presence of a solid acid catalyst to form 2,2-dimethyl-1,3-dioxolane and b) hydrolyzing the 2,2-dimethyl-1,3-dioxolane with water in the presence of a solid acid catalyst to form monoethylene glycol.

2. The process of claim 1, wherein the catalyst used in step a) is an acid activated clay.

3. The process of claim 1 or 2, wherein the mole ratio of acetone/ethylene oxide ranges from about 1:1 to about 5:1.

4. The process of claim 1 wherein the reaction temperature ranges from about 30° C. to about 80° C.

5. The process of claims 1 wherein prior to step b) the 2,2-dimethyl-1,3-dioxolane is distilled.

6. The process of claims 1 or 2, wherein the 2,2-dimethyl-1,3-dioxolane is hydrolyzed in step b) with water in the presence of a solid acid catalyst selected from an ion-exchange resin and an acid activated clay.

7. The process of claim 6 wherein a substantially stoichiometric amount of water is used for hydrolyzing 2,2-dimethyl-1,3-dioxolane.

8. The process of claim 1 wherein the acetone is distilled off during the reaction in step b).

* * * * *